(12) United States Patent
Dhawan et al.

(10) Patent No.: US 12,018,222 B2
(45) Date of Patent: *Jun. 25, 2024

(54) SYNTHETIC LUBRICITY ADDITIVES FOR HYDROCARBON FUELS

(71) Applicant: Ecolab USA Inc., St. Paul, MN (US)

(72) Inventors: Ashish Dhawan, Aurora, IL (US); Xiaojin Harry Li, Bartlett, IL (US); Nestor U. Soriano, Jr., Missouri City, TX (US); Karina Eureste, Houston, TX (US)

(73) Assignee: ECOLAB USA INC., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/223,694

(22) Filed: Jul. 19, 2023

(65) Prior Publication Data

US 2023/0365882 A1 Nov. 16, 2023

Related U.S. Application Data

(63) Continuation of application No. 17/744,229, filed on May 13, 2022, now Pat. No. 11,746,302.

(60) Provisional application No. 63/188,095, filed on May 13, 2021.

(51) Int. Cl.
*C10L 10/08* (2006.01)
*C07D 207/12* (2006.01)

(52) U.S. Cl.
CPC ............ *C10L 10/08* (2013.01); *C07D 207/12* (2013.01); *C10L 2200/0446* (2013.01)

(58) Field of Classification Search
CPC ... C07D 207/404; C10L 1/2383; C10L 1/232; C10L 10/08; C10L 10/04; C10L 2200/0446; C10L 2200/0469
See application file for complete search history.

(56) References Cited

U.S. PATENT DOCUMENTS

| | | | |
|---|---|---|---|
| 4,102,798 A | 7/1978 | Ryer et al. | |
| 4,240,970 A | 12/1980 | Chibnik | |
| 4,292,186 A | 9/1981 | Chibnik et al. | |
| 4,652,273 A | 3/1987 | Maldonado et al. | |
| 4,675,374 A | 6/1987 | Nichols | |
| 4,747,964 A | 5/1988 | Durand et al. | |
| 4,997,456 A | 3/1991 | Malfer | |
| 5,032,145 A | 7/1991 | Axelrod et al. | |
| 5,047,160 A | 9/1991 | Emert et al. | |
| 5,241,003 A | 8/1993 | Degonia et al. | |
| 5,324,334 A | 6/1994 | Brois et al. | |
| 5,551,957 A | 9/1996 | Cunningham et al. | |
| 6,127,321 A | 10/2000 | Emert | |
| 6,419,714 B2 | 7/2002 | Thompson et al. | |
| 6,548,458 B2 | 4/2003 | Loper | |
| 7,182,795 B2 | 2/2007 | Henly et al. | |
| 7,208,022 B2 | 4/2007 | Corkwell et al. | |
| 7,361,629 B2 | 4/2008 | Oper et al. | |
| 7,615,521 B2 | 11/2009 | Eveland et al. | |
| 8,939,125 B2 | 1/2015 | Bardasz | |
| 9,598,655 B2 | 3/2017 | Shaikh et al. | |
| 10,023,819 B2 | 7/2018 | Stevenson et al. | |
| 10,260,019 B2 | 4/2019 | Perera et al. | |
| 2003/0172584 A1 | 9/2003 | Henly et al. | |
| 2019/0169514 A1 | 6/2019 | Smith et al. | |

FOREIGN PATENT DOCUMENTS

EP 1348754 A2 10/2003

OTHER PUBLICATIONS

Seung-Yeob Baek, et al., "Synthesis of Succinic Acid Alkyl Half-Ester Derivatives with Improved Lubricity Characteristics" Ind. Eng. Chem. Res. 2012, 51, 3564-3568.
Andrea Pucci, et al., "Aggregation Induced Luminescence of Poly(Isobutene) Succinic Anhydrides and Imides" Polymer Preprints 2007, 48(2),229-230.
PCT/US2022/029166, International Search Report and Written Opinion, Sep. 1, 2022, 8 pgs.

*Primary Examiner* — Vishal V Vasisth
(74) *Attorney, Agent, or Firm* — Kagan Binder, PLLC

(57) ABSTRACT

Lubricity additives for hydrocarbon fuels are presented according to formula I:

$$R^1[(-O-R^2)_n-Q]_p \qquad (I)$$

wherein p is 3 or greater; each n is independently selected from integers equal to 2 or greater; $R^1$ is a C3-C20 aliphatic hydrocarbon group of valence p which is branched or linear and which is substituted or unsubstituted; each $R^2$ is independently selected from C2-C20 divalent aliphatic or aromatic hydrocarbon groups which are branched or linear and which are substituted or unsubstituted; and each Q is independently selected from —$NH_2$ or a moiety according to formula II:

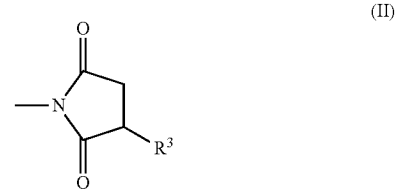

wherein each $R^3$ is independently selected from C8-C60 alkenyl groups which are substituted or unsubstituted, providing that at least one Q is the moiety according to formula II.

19 Claims, No Drawings

SYNTHETIC LUBRICITY ADDITIVES FOR HYDROCARBON FUELS

CROSS REFERENCE TO RELATED APPLICATIONS

This application is a continuation application of U.S. Ser. No. 17/744,229, now patent Ser. No. 11/746,302, filed May 13, 2022, which in turn claims the benefit of U.S. Provisional Patent Application Ser. No. 63/188,095, filed May 13, 2021, the disclosures of which are disclosure of which is herein incorporated by reference in their entirety.

FIELD OF THE DISCLOSURE

This disclosure relates to lubricity additives for hydrocarbon fuels, including adducts of alkenyl succinic anhydrides (ASA's) and certain polyamines which include polyether moieties.

BACKGROUND OF THE DISCLOSURE

Refiners utilize intensive fuel processing in order to meet the stringent government mandates limiting permissible levels of sulfur in finished fuels. At present in the United States, the maximum specification for ultra-low sulfur diesel (ULSD) is 15 ppm. USLD is the on-road diesel fuel in the US. Unfortunately, this intensive processing also eliminates trace oxygen and nitrogen compounds that contribute to the fuel's inherent lubricity. Hence ULSD is known to be less lubricating if not treated with lubricity improving additives. Lubrication is vital in preventing wear in fuel delivery systems, particularly in pumps, high pressure pumps, and injectors.

The majority of commercial lubricity additives are based on fatty acids of natural origin such as vegetable oils or plant oils, such as tall oil fatty acids (TOFA). As such, these lubricity additives are subjected to supply and cost constraints due to the inherent price volatility of these raw materials. Moreover, variabilities in qualities and properties of vegetable and plant-based oils in various regions create product quality inconsistencies. Hence, the development of 100% synthetic-based lubricity additives holds the potential to ease supply chain challenges, avoid significant raw material cost fluctuations, and ensure consistent product quality.

In addition to lubricity additives, hydrocarbon fuels such as diesel fuel may be formulated with additives to modify other characteristics of the fuel and its performance in an engine. Such additives may include dispersants, antioxidants, viscosity index modifiers, corrosion inhibitors, and the like.

U.S. Pat. No. 7,361,629 concerns a composition for use as an additive for fuels and lubricants that includes an amination product of a hydrocarbyl substituted succinic acylating agent and polyamines. U.S. Pat. No. 7,361,629 teaches the use of this additive as a dispersant to maintain impurities and deposits in a suspended state so that they can be removed from the system by filtration or other means rather than being deposited on internal engine components.

U.S. Pat. No. 5,551,957 concerns a fuel additive concentrate for use as a detergent/dispersant. The fuel additive concentrate includes a fuel-soluble product formed by reaction between (a) at least one polyamine and (b) at least one acyclic hydrocarbyl-substituted succinic acylating agent.

SUMMARY OF THE DISCLOSURE

Briefly, the present disclosure provides lubricity additives according to formula I:

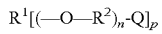

wherein p is 3 or greater; each n is independently selected from integers equal to 2 or greater; $R^1$ is a C3-C20 aliphatic hydrocarbon group of valence p which is branched or linear and which is substituted or unsubstituted; each $R^2$ is independently selected from C2-C20 divalent aliphatic or aromatic hydrocarbon groups which are branched or linear and which are substituted or unsubstituted; and each Q is independently selected from —$NH_2$ or a moiety according to formula II:

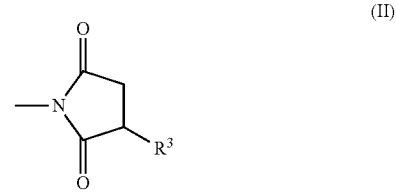

wherein each $R^3$ is independently selected from C8-C60 alkenyl groups which are substituted or unsubstituted, providing that at least one Q is the moiety according to formula II. In some embodiments, at least two Q's are moieties according to formula II. In various embodiments, each n is independently selected from integers from 2-40 inclusive, from 2-20 inclusive, or from 2-8 inclusive. In various embodiments, each $R^2$ is independently selected from C2-C6, C2-C4, or C2-C3 divalent aliphatic hydrocarbon groups or from the group consisting of —$CH_2CH_2$—, —CH($CH_3$)$CH_2$—, —$CH_2CH(CH_3)$—, and —CH(Ph)—$CH_2$—. In various embodiments, $R^1$ is selected from C3-C12 aliphatic hydrocarbon groups or C3-C6 aliphatic hydrocarbon groups. Additional embodiments of the lubricity additives of the present disclosure are described below.

In another aspect, the present disclosure provides fuel mixtures comprising a hydrocarbon fuel; and a lubricity additive according to the present disclosure. In various embodiments the hydrocarbon fuel may be a middle distillate fuel, derived from petroleum or biobased feedstock. Additional embodiments of the fuel mixtures of the present disclosure are described below.

In another aspect, the present disclosure provides methods of making lubricity additives comprising reacting an alkenyl succinic anhydride according to formula III:

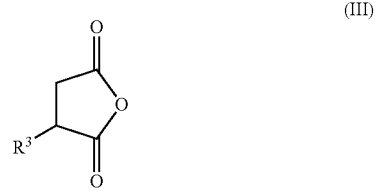

with a species according to formula IV:

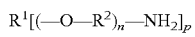

wherein p is 3 or greater; each n is independently selected from integers equal to 2 or greater; $R^1$ is a C3-C20 aliphatic hydrocarbon group of valence p which is branched or linear and which is substituted or unsubstituted; each $R^2$ is independently selected from C2-C20 divalent aliphatic or aromatic hydrocarbon groups which are branched or linear and which are substituted or unsubstituted; and each $R^3$ is independently selected from C8-C60 alkenyl groups which are substituted or unsubstituted. Additional embodiments of the methods of the present disclosure are described below.

The preceding summary of the present disclosure is not intended to describe each embodiment of the present invention. The details of one or more embodiments of the invention are also set forth in the description below. Other features, objects, and advantages of the invention will be apparent from the description and from the claims.

In this application:

"common solvents" refers to low molecular weight organic liquids commonly used as solvents by practitioners in the art, which may include aliphatic and alicyclic hydrocarbons (e.g., hexane, heptane, and cyclohexane), aromatic solvents (e.g., benzene, toluene, xylene, and mixtures of heavy aromatic naphtha), ethers (e.g., diethyl ether, glyme, diglyme, diisopropyl ether, and tetrahydrofuran), esters (e.g., ethyl acetate and butyl acetate), alcohols (e.g., ethanol and isopropyl alcohol), ketones (e.g., acetone, methyl ethyl ketone, and methyl isobutyl ketone), sulfoxides (e.g., dimethyl sulfoxide), amides (e.g., N,N-dimethylformamide, N,N-dimethylacetamide, and N-methyl-2-pyrrolidone), halogenated solvents (e.g., methylchloroform, 1,1,2-trichloro-1,2,2-trifluoroethane, trichloroethylene, and trifluorotoluene), and mixtures thereof, and "substituted" means, for a chemical species, group or moiety, substituted by conventional substituents which do not interfere with the desired product or process, e.g., substituents can be alkyl, alkoxy, aryl, phenyl, halo (F, Cl, Br, I), cyano, nitro, etc.

All scientific and technical terms used herein have meanings commonly used in the art unless otherwise specified. All chemical formulas used herein are intended to include all enantiomers or stereoisomers unless otherwise specified.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising," and the like.

DETAILED DESCRIPTION

The present disclosure provides synthetic lubricity additives for hydrocarbon fuels such as diesel fuel. Lubricity additives may be species according to formula I.

wherein p is 3 or greater; wherein each n is independently selected from integers equal to 2 or greater; wherein $R^1$ is a C3-C20 aliphatic hydrocarbon group of valence p which is branched or linear and which is substituted or unsubstituted; wherein each $R^2$ is independently selected from C2-C20 divalent aliphatic or aromatic hydrocarbon groups which are branched or linear and which are substituted or unsubstituted; and wherein each Q is independently selected from —NH$_2$ or a moiety according to formula II:

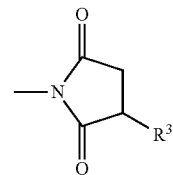

wherein each $R^3$ is independently selected from C8-C60 alkenyl groups which are substituted or unsubstituted, providing that at least one Q is the moiety according to formula II.

In some embodiments, p is 3 or p is 4.

In various embodiments, each n may be independently selected from integers equal to or greater than 2, 3, 4, 5, 6, 8, or 10. In any such embodiments, n optionally may be limited to not greater than 40, 30, 20, 15, 10, or 8.

In some embodiments, $R^1$ may be selected from straight-chain, branched, or cyclic aliphatic hydrocarbon groups of valence p. In various embodiments, $R^1$ may be selected from C3-C20 groups, C3-C16 groups, C3-C12 groups, C3-C8 groups, C4-C20 groups, C4-C16 groups, C4-C12 groups, C4-C8 groups, C5-C20 groups, C5-C16 groups, C5-C12 groups, C5-C8 groups, C6-C20 groups, C6-C16 groups, C6-C12 groups, or C6-C8 groups.

In various embodiments, each $R^2$ may be independently selected from C2-C20 divalent aliphatic or aromatic hydrocarbon groups which are branched or linear and which are substituted or unsubstituted. In various embodiments, each $R^2$ group may be independently selected from C2-C16 groups, C2-C12 groups, C2-C8 groups, C2-C6 groups, C2-C5 groups, C2-C4 groups, or C2-C3 groups. In some embodiments, each $R^2$ group may be independently selected from —CH$_2$CH$_2$—, —CH(CH$_3$)CH$_2$—, —CH$_2$CH(CH$_3$)—, —CH$_2$CH$_2$CH$_2$—, —CH(CH$_3$)CH$_2$CH$_2$—, —CH$_2$CH(CH$_3$)CH$_2$—, —CH$_2$CH$_2$CH(CH$_3$)—, or —CH(Ph)—CH$_2$—.

In various embodiments, each $R^3$ may be independently selected from straight-chain, branched, or cyclic groups. Each $R^3$ may attach to the succinyl group of Formula II at a terminal carbon of the $R^3$ group, or may attach to the succinyl group at a non-terminal carbon of the $R^3$ group such that the $R^3$ group branches at that carbon. In various embodiments, each $R^3$ group may be independently selected from C8-C60 alkenyl groups, C10-C60 alkenyl groups, C12-C60 alkenyl groups, C14-C60 alkenyl groups, C16-C60 alkenyl groups, C18-C60 alkenyl groups, C20-C60 alkenyl groups, C21-C60 alkenyl groups, C8-C50 alkenyl groups, C10-C50 alkenyl groups, C12-C50 alkenyl groups, C14-C50 alkenyl groups, C16-C50 alkenyl groups, C18-C50 alkenyl groups, C20-C50 alkenyl groups, C21-C50 alkenyl groups, C8-C40 alkenyl groups, C10-C40 alkenyl groups, C12-C40 alkenyl groups, C14-C40 alkenyl groups, C16-C40 alkenyl groups, C18-C40 alkenyl groups, C20-C40 alkenyl groups, C21-C40 alkenyl groups, C8-C32 alkenyl groups, C10-C32 alkenyl groups, C12-C32 alkenyl groups, C14-C32 alkenyl groups, C16-C32 alkenyl groups, C18-C32 alkenyl groups, C20-C32 alkenyl groups, C21-C32 alkenyl groups, C8-C28 alkenyl groups, C10-C28 alkenyl groups, C12-C28 alkenyl groups, C14-C28 alkenyl groups, C16-C28 alkenyl groups, C18-C28 alkenyl groups, C20-C28 alkenyl groups, C21-C28 alkenyl groups, C8-C24 alkenyl groups, C10-C24 alkenyl groups, C12-C24 alkenyl groups, C14-C24 alkenyl groups, C16-C24 alkenyl groups, C18-C24 alkenyl groups, C20-C24 alkenyl groups, or C21-C24 alkenyl groups.

Among lubricity additives according to the present disclosure having $R^3$ groups in the range of C12-C24, it is believed that the longer-chain $R^3$ groups may provide more effective lubricity additives.

The present lubricity additives may be made by any suitable method. In one method, an alkenyl succinic anhydride (ASA) according to formula III:

$$\text{(III)}$$

[Structure: succinic anhydride ring with $R^3$ substituent]

is reacted with a species according to formula IV:

$$R^1[(-O-R^2)_n-NH_2]_p \qquad \text{(IV)}$$

wherein $R^1$, $R^2$, $R^3$, n, and p are as described above. The species according to formula IV is a polyamine having p terminal amine groups and including polyether moieties represented by $(-O-R^2)_n$.

The alkenyl succinic anhydride (ASA) according to formula III may be made according to any suitable method. In one embodiment, a selected olefin is reacted with maleic anhydride under inert atmosphere at elevated temperature, as described below in the Examples. The selected olefin may be present in a slight molar excess to minimize the formation of polymaleic anhydride. The olefin may be an alpha olefin or an internal olefin having a carbon-carbon double bond available for reaction. The selected olefin may be a single species of olefin or a mixture of species.

The ASA may be reacted with the species according to formula IV by any suitable method. In one embodiment, the two reactants are reacted under inert atmosphere at elevated temperature, as described below in the Examples. The ASA and the species according to formula IV may be present in the reaction mixture in a molar ratio of at least about 1:1, at least about 1.5:1, at least about 2:1, at least about 2.5:1, or at least about 3:1. Typically the ASA and the species according to formula IV are present in the reaction mixture in a molar ratio of about 2:1. In one embodiment, the reaction temperature is increased stepwise to provide amidation of ASA at lower temperatures, followed by ring closure to provide the corresponding imide groups at higher temperatures. Stepwise amidation and imidation was found to eliminate the formation of precipitates resulting from side-reactions.

The present fuel additives may be provided neat or in solution. Certain fuel additives may be gels or solids at room temperature in the absence of solvent, leading to difficulty in handling and in blending with fuel. For example, neat ASA/polyamine adducts are gels or solids at room temperature, depending on the length and the structure (e.g., branched or straight) of the alkenyl R groups. Formulations of these lubricity additives with as little as 10% solvent may remain liquid and stable (i.e., no gelation, precipitation, phase separation, or dramatic increase in viscosity) during prolonged storage at 10° C. Any suitable common solvent may be used. In some embodiments, the solvent is an aromatic solvent such as heavy aromatic naphtha. Greater dilution may result in reduced viscosity and therefore improved pumpability at lower temperatures. Formulations of these lubricity additives with 20% solvent, 30% solvent, or 50% solvent may demonstrate low viscosity at sub-zero (centigrade) temperatures and excellent performance as lubricity additives.

The present disclosure additionally provides fuel mixtures comprising a hydrocarbon fuel and a lubricity additive according to the present disclosure. Any suitable fuel may be used. In various embodiments, the hydrocarbon fuel may be a middle distillate fuel, a bio-sourced fuel, or a diesel fuel. The fuel mixture may additionally comprise other additives such as one or more of dispersants, antioxidants, viscosity index modifiers, corrosion inhibitors, and the like.

Additional embodiments are recited in the Selected Embodiments and Examples below.

SELECTED EMBODIMENTS

The following embodiments, designated by letter and number, are intended to further illustrate the present disclosure but should not be construed to unduly limit this disclosure.

A1. A lubricity additive according to formula I:

$$R^1[(-O-R^2)_n\text{-}Q]_p \qquad \text{(I)}$$

wherein p is 3 or greater;
wherein each n is independently selected from integers equal to 2 or greater;
wherein $R^1$ is a C3-C20 aliphatic hydrocarbon group of valence p which is branched or linear and which is substituted or unsubstituted;
wherein each $R^2$ is independently selected from C2-C20 divalent aliphatic or aromatic hydrocarbon groups which are branched or linear and which are substituted or unsubstituted; and
wherein each Q is independently selected from $-NH_2$ or a moiety according to formula II:

$$\text{(II)}$$

[Structure: succinimide ring with N and $R^3$ substituent]

wherein each $R^3$ is independently selected from C8-C60 alkenyl groups which are substituted or unsubstituted, providing that at least one Q is the moiety according to formula II.

A2. A lubricity additive according to embodiment A1 wherein at least two Q's are moieties according to formula II.

A3. A lubricity additive according to embodiment A1 wherein two Q's are moieties according to formula II and one Q is $-NH_2$.

A4. A lubricity additive according to any of embodiments A1-A3 or wherein p is 3 or 4.

A5. A lubricity additive according to any of embodiments A1-A3 wherein p is 3.

A6. A lubricity additive according to any of embodiments A1-A5 wherein each n is independently selected from integers from 2-40 inclusive.

A7. A lubricity additive according to any of embodiments A1-A5 wherein each n is independently selected from integers from 2-20 inclusive.

A8. A lubricity additive according to any of embodiments A1-A5 wherein each n is independently selected from integers from 2-8 inclusive.
A9. A lubricity additive according to any of embodiments A1-A5 wherein each n is independently selected from integers from 4-40 inclusive.
A10. A lubricity additive according to any of embodiments A1-A5 wherein each n is independently selected from integers from 4-20 inclusive.
A11. A lubricity additive according to any of embodiments A1-A5 wherein each n is independently selected from integers from 4-8 inclusive.
A12. A lubricity additive according to any of embodiments A1-A11 wherein each $R^2$ is independently selected from C2-C6 divalent aliphatic hydrocarbon groups which are branched or linear and which are substituted or unsubstituted.
A13. A lubricity additive according to any of embodiments A1-A11 wherein each $R^2$ is independently selected from C2-C4 divalent aliphatic hydrocarbon groups which are branched or linear and which are substituted or unsubstituted.
A14. A lubricity additive according to any of embodiments A1-A11 wherein each $R^2$ is independently selected from C2-C3 divalent aliphatic hydrocarbon groups which are branched or linear and which are substituted or unsubstituted.
A15. A lubricity additive according to any of embodiments A1-A11 wherein each $R^2$ is independently selected from the group consisting of —$CH_2CH_2$—, —$CH(CH_3)CH_2$—, —$CH_2CH(CH_3)$—, and —CH(Ph)—$CH_2$—.
A16. A lubricity additive according to any of embodiments A1-A11 wherein each $R^2$ is independently selected from the group consisting of —$CH_2CH_2$—, —$CH(CH_3)CH_2$—, and —$CH_2CH(CH_3)$—.
A17. A lubricity additive according to any of embodiments A1-A11 wherein each $R^2$ is —CH(Ph)—$CH_2$—.
A18. A lubricity additive according to any of embodiments A1-A11 wherein each $R^2$ is independently selected from the group consisting of —$CH(CH_3)CH_2$— and —$CH_2CH(CH_3)$—.
A19. A lubricity additive according to any of embodiments A1-A18 wherein $R^1$ is selected from C3-C12 aliphatic hydrocarbon groups of valence p which are branched or linear and which are substituted or unsubstituted.
A20. A lubricity additive according to any of embodiments A1-A18 wherein $R^1$ is selected from C3-C6 aliphatic hydrocarbon groups of valence p which are branched or linear and which are substituted or unsubstituted.
F1. A fuel mixture comprising:
  a) a hydrocarbon fuel; and
  b) a lubricity additive according to any of embodiments 1-14.
F2. A fuel mixture according to embodiment F1 wherein the hydrocarbon fuel is a middle distillate fuel.
F3. A fuel mixture according to embodiment F1 wherein the hydrocarbon fuel is a diesel fuel.
F4. A fuel mixture according to embodiment F1 wherein the hydrocarbon fuel is a diesel fuel derived from petroleum or biobased feedstock.
F5. A fuel mixture according to embodiment F1 wherein the hydrocarbon fuel is a bio-based fuel.

M1. A method of making a lubricity additive comprising reacting an alkenyl succinic anhydride according to formula III:

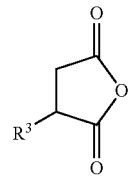

(III)

with a species according to formula IV:

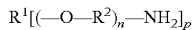

(IV)

wherein p is 3 or greater;
  wherein each n is independently selected from integers equal to 2 or greater;
  wherein $R^1$ is a C3-C20 aliphatic hydrocarbon group of valence p which is branched or linear and which is substituted or unsubstituted;
  wherein each $R^2$ is independently selected from C2-C20 divalent aliphatic or aromatic hydrocarbon groups which are branched or linear and which are substituted or unsubstituted; and
  wherein each $R^3$ is independently selected from C8-C60 alkenyl groups which are substituted or unsubstituted.
M2. A method according to embodiment M1 wherein the alkenyl succinic anhydride according to formula III is reacted with the species according to formula IV at a molar ratio of at least about 1:1.
M3. A method according to embodiment M1 wherein the alkenyl succinic anhydride according to formula III is reacted with the species according to formula IV at a molar ratio of at least about 2:1.
M4. A method according to any of embodiments M1-M3 or wherein p is 3 or 4.
M5. A method according to any of embodiments M1-M3 wherein p is 3.
M6. A method according to any of embodiments M1-M5 wherein each n is independently selected from integers from 2-40 inclusive.
M7. A method according to any of embodiments M1-M5 wherein each n is independently selected from integers from 2-20 inclusive.
M8. A method according to any of embodiments M1-M5 wherein each n is independently selected from integers from 2-8 inclusive.
M9. A method according to any of embodiments M1-M5 wherein each n is independently selected from integers from 4-40 inclusive.
M10. A method according to any of embodiments M1-M5 wherein each n is independently selected from integers from 4-20 inclusive.
M11. A method according to any of embodiments M1-M5 wherein each n is independently selected from integers from 4-8 inclusive.
M12. A method according to any of embodiments M1-M11 wherein each $R^2$ is independently selected from C2-C6 divalent aliphatic hydrocarbon groups which are branched or linear and which are substituted or unsubstituted.
M13. A method according to any of embodiments M1-M11 wherein each $R^2$ is independently selected from C2-C4 divalent aliphatic hydrocarbon groups which are branched or linear and which are substituted or unsubstituted.

M14. A method according to any of embodiments M1-M11 wherein each $R^2$ is independently selected from C2-C3 divalent aliphatic hydrocarbon groups which are branched or linear and which are substituted or unsubstituted.

M15. A method according to any of embodiments M1-M11 wherein each $R^2$ is independently selected from the group consisting of —$CH_2CH_2$—, —$CH(CH_3)CH_2$—, —$CH_2CH(CH_3)$—, and —$CH(Ph)CH_2$—.

M16. A method according to any of embodiments M1-M11 wherein each $R^2$ is independently selected from the group consisting of —$CH_2CH_2$—, —$CH(CH_3)CH_2$—, and —$CH_2CH(CH_3)$—.

M17. A method according to any of embodiments M1-M11 wherein each $R^2$ is —$CH(Ph)$-$CH_2$—.

M18. A method according to any of embodiments M1-M11 wherein each $R^2$ is independently selected from the group consisting of —$CH(CH_3)CH_2$— and —$CH_2CH(CH_3)$—.

M19. A method according to any of embodiments M1-M18 wherein $R^1$ is selected from C3-C12 aliphatic hydrocarbon groups of valence p which are branched or linear and which are substituted or unsubstituted.

M20. A method according to any of embodiments M1-M18 wherein $R^1$ is selected from C3-C6 aliphatic hydrocarbon groups of valence p which are branched or linear and which are substituted or unsubstituted.

M21. A method according to any of embodiments M1-M20 wherein the lubricity additive is a lubricity additive according to any of embodiments A1-A14.

Objects and advantages of this disclosure are further illustrated by the following examples, but the particular materials and amounts thereof recited in these examples, as well as other conditions and details, should not be construed to unduly limit this disclosure.

EXAMPLES

Unless otherwise noted, all reagents were obtained or are available from Aldrich Chemical Co., Milwaukee, WI, (Aldrich) or may be synthesized by known methods.

All parts, percentages, ratios, etc. in the examples and the rest of the specification are by weight, unless noted otherwise. The following abbreviations may be used: m=meters; cm=centimeters; mm=millimeters; um=micrometers; ft=feet; in =inch; RPM=revolutions per minute; kg=kilograms; oz=ounces; lb=pounds; Pa=Pascals; sec=seconds; min=minutes; hr=hours; and RH=relative humidity. The terms "weight %", "% by weight", and "wt %" are used interchangeably.

Materials

| Designation | Description |
| --- | --- |
| heavy aromatic naphtha | heavy aromatic naphtha obtained from ExxonMobil Chemical, USA, under the brand name SOLVESSO ™ 150. |
| i-octadecenyl-succinicanhydride (iODSA) | i-Octadecenyl-succinicanhydride obtained from Dixie Chemical Company, USA, under designation ODSA. |
| T-403 | Trimethylolpropane tris[poly(propylene glycol), amine terminated] ether, CAS 39423-51-3, obtained from Aldrich |

| Designation | Description |
| --- | --- |
| | under the chemical trade name Jeffamine ® T-403 Polyetheramine. |
| ethylenediamine | Ethylenediamine, CAS 107-15-3, obtained from Aldrich under the designation 1,2-Ethylenediamine (EDA). |
| diaminopropane | Diaminopropane, CAS 109-76-2, obtained from Aldrich under the designation 1,3-Diaminopropane. |
| diaminohexane | Diaminohexane, CAS 124-09-4, obtained from Aldrich under the designation 1,6-diaminohexane. |
| ULSD | Ultra-Low Sulfur Diesel fuel, Winter Export formulation. |

Synthesis of ASA/Polyamine Adducts

To a 250 mL three-necked round-bottom flask equipped with a temperature probe, nitrogen inlet, Dean-Stark apparatus, condenser and magnetic stir bar was added i-octadecenylsuccinicanhydride (iODSA) via one of the necks. Polyamine (T-403 or comparative polyamines ethylenediamine, 1,3-diaminopropane, or 1,6-diaminohexane) was then charged to the well-stirred reaction mixture in a 2:1 ASA/polyamine molar ratio. The resulting mixture was heated gradually to 120° C. with nitrogen blanketing, then heated up to 150° C. with nitrogen purging, and stirred at 150° C. with nitrogen purging for 3 to 5 hours or until completion of the reaction to result in the desired product. A portion of the product was formulated to 70% or 80% actives by weight with heavy aromatic naphtha solvent in a glass jar, and the formulated product was put in a 6 to 8° C. fridge for at least 7 days for a product storage stability test. After finishing and passing the product stability test, the formulated product was used for lubricity performance evaluation (HFRR test).

High Frequency Reciprocating Rig (HFRR) Test Method

HFRR testing was performed in accordance with ASTM D6079 Standard Test Method for Evaluating Lubricity of Diesel Fuels by the High-Frequency Reciprocating Rig (HFRR).

HFRR Results

Example 1 and Comparative Examples 2C-5C

Table I reports HFRR results demonstrating lubricity improvement (smaller wear scar) with the use of the iODSA/T-403 adduct (Example 1) than with the use of comparative iODSA/diamine adducts (Comparative Examples C3-C5) or no additive (Comparative Example C2). All additive formulations were 80% by weight additive in heavy aromatic naphtha. The indicated additive formulation was used to treat ULSD fuels at a concentration of 200 ppm (inclusive of additive and solvent in the additive formulation) and tested in accordance with the HFRR Test Method.

TABLE I

| Example | Adduct (200 ppm) | Wear Scar (μm) |
| --- | --- | --- |
| 1 | iODSA/T-403 | 429 |
| 2C | -none- | 558 |
| 3C | iODSA/ethylenediamine | 597 |
| 4C | iODSA/diaminopropane | 537 |
| 5C | iODSA/diaminohexane | 554 |

Various modifications and alterations of this disclosure will become apparent to those skilled in the art without departing from the scope and principles of this disclosure, and it should be understood that this disclosure is not to be unduly limited to the illustrative embodiments set forth hereinabove.

We claim:

1. A method of improving fuel lubricity performance comprising adding to a hydrocarbon fuel a lubricity additive according to formula I:

wherein p is 3 or greater;
wherein each n is independently selected from integers equal to 2 or greater;
wherein $R^1$ is a C3-C20 aliphatic hydrocarbon group of valence p which is branched or linear and which is substituted or unsubstituted;
wherein each $R^2$ is independently selected from C2-C20 divalent aliphatic or aromatic hydrocarbon groups which are branched or linear and which are substituted or unsubstituted; and
wherein each Q is independently selected from —$NH_2$ or a moiety according to formula II:

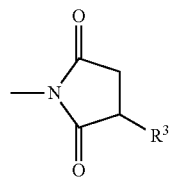

wherein each $R^3$ is independently selected from C8-C60 alkenyl groups which are substituted or unsubstituted, providing that at least one Q is the moiety according to formula II.

2. The method according to claim 1 wherein at least two Q's are moieties according to formula II.

3. The method according to claim 1 or wherein p is 3 or 4.

4. The method according to claim 1 wherein p is 3.

5. The method according to claim 1 wherein each n is independently selected from integers from 2-40 inclusive.

6. The method according to claim 1 wherein each n is independently selected from integers from 2-20 inclusive.

7. The method according to claim 1 wherein each n is independently selected from integers from 2-8 inclusive.

8. The method according to claim 1 wherein each $R^2$ is independently selected from C2-C6 divalent aliphatic hydrocarbon groups which are branched or linear and which are substituted or unsubstituted.

9. The method according to claim 1 wherein each $R^2$ is independently selected from C2-C4 divalent aliphatic hydrocarbon groups which are branched or linear and which are substituted or unsubstituted.

10. The method according to claim 1 wherein each $R^2$ is independently selected from C2-C3 divalent aliphatic hydrocarbon groups which are branched or linear and which are substituted or unsubstituted.

11. The method according to claim 1 wherein each $R^2$ is independently selected from the group consisting of —$CH_2CH_2$—, —$CH(CH_3)CH_2$—, —$CH_2CH(CH_3)$—, and —CH(Ph)—$CH_2$—.

12. The method according to claim 1 wherein each $R^2$ is independently selected from the group consisting of —CH($CH_3$)$CH_2$— and —$CH_2$CH($CH_3$)—.

13. The method according to claim 1 wherein 10 is selected from C3-C12 aliphatic hydrocarbon groups of valence p which are branched or linear and which are substituted or unsubstituted.

14. The method according to claim 1 wherein 10 is selected from C3-C6 aliphatic hydrocarbon groups of valence p which are branched or linear and which are substituted or unsubstituted.

15. The method according to claim 1 wherein the hydrocarbon fuel is a middle distillate fuel.

16. The method according to claim 1 wherein the hydrocarbon fuel is a diesel fuel.

17. The method according to claim 1 wherein the hydrocarbon fuel is an ultra-low sulfur diesel fuel.

18. The method according to claim 1 wherein the hydrocarbon fuel is a diesel fuel derived from petroleum or biobased feedstock.

19. The method according to claim 1 wherein the hydrocarbon fuel is a bio-based fuel.

* * * * *

UNITED STATES PATENT AND TRADEMARK OFFICE
CERTIFICATE OF CORRECTION

PATENT NO. : 12,018,222 B2
APPLICATION NO. : 18/223694
DATED : June 25, 2024
INVENTOR(S) : Ashish Dhawan et al.

It is certified that error appears in the above-identified patent and that said Letters Patent is hereby corrected as shown below:

On the Title Page

Item [56] In References Cited, Column 2, 6th entry, "Oper et al." should be --of Loper et al.--.

In the Specification

Column 1, Line 10, "disclosure of which is" should be deleted.

In the Claims

Column 12, Claim 13, Line 24, "wherein 10" should be --wherein $R^1$--.

Column 12, Claim 14, Line 28, "wherein 10" should be --wherein $R^1$--.

Signed and Sealed this
Twenty-fourth Day of September, 2024

Katherine Kelly Vidal
*Director of the United States Patent and Trademark Office*